United States Patent [19]
Estes

[11] Patent Number: 5,693,053
[45] Date of Patent: Dec. 2, 1997

[54] VARIABLE ANGLE AND TRANSITIONAL LINKING MEMBER

[75] Inventor: Bradley T. Estes, Memphis, Tenn.

[73] Assignee: SDGI Holdings, Inc., Memphis, Tenn.

[21] Appl. No.: 545,211

[22] Filed: Oct. 19, 1995

[51] Int. Cl.⁶ .................................... A61B 17/70
[52] U.S. Cl. ................... 606/61; 606/63; 606/64; 606/72; 606/73
[58] Field of Search .................. 606/60, 61, 63, 606/64, 72, 73

[56] References Cited

U.S. PATENT DOCUMENTS

| | | | |
|---|---|---|---|
| 4,641,636 | 2/1987 | Cotrel . | |
| 4,773,402 | 9/1988 | Asher et al. . | |
| 4,790,297 | 12/1988 | Luque . | |
| 4,987,892 | 1/1991 | Krag et al. . | |
| 5,030,220 | 7/1991 | Howland | 606/61 |
| 5,084,049 | 1/1992 | Asher et al. | 606/61 |
| 5,092,893 | 3/1992 | Smith | 623/17 |
| 5,102,412 | 4/1992 | Rogozinski | 606/61 |
| 5,108,395 | 4/1992 | Laurain . | |
| 5,127,912 | 7/1992 | Ray et al. | 606/61 |
| 5,133,717 | 7/1992 | Chopin | 606/61 |
| 5,147,360 | 9/1992 | Dubousset | 606/61 |
| 5,154,718 | 10/1992 | Cozad | 606/61 |
| 5,261,909 | 11/1993 | Sutterlin et al. . | |
| 5,261,913 | 11/1993 | Marnay | 606/61 |
| 5,282,801 | 2/1994 | Sherman . | |
| 5,312,405 | 5/1994 | Korotko et al. | 606/61 |
| 5,334,203 | 8/1994 | Wagner | 606/61 |
| 5,549,607 | 8/1996 | Olson et al. | 606/61 |

FOREIGN PATENT DOCUMENTS

| | | |
|---|---|---|
| 3219575 A1 | 12/1983 | Germany . |
| 780652 | 8/1957 | United Kingdom . |
| 2090745 | 7/1982 | United Kingdom . |
| WO 90/04948 | 5/1990 | WIPO . |

OTHER PUBLICATIONS

*TSRH Crosslink Components,* Danek Medical, 1990.
*TSRH Lumbar System,* Danek Medical, 1991.
*Alpha Spinal System,* Alphatec Manufacturing, Inc. no date.
*Universal Instrumentation* (CD) *for Spinal Surgery,* Stuart; Dr. Cotrel/Dr. Dubousset, 1985.
Charles M. Ruland, M.D., Paul C. McAfee, M.D., Karen E. Warden, and Bryan W. Cunningham, *Triangulation of Pedicular Instrumentation—A Biomechanical Analysis,* Nov. 1990.

*Primary Examiner*—Michael Buiz
*Assistant Examiner*—Daphja Shai
*Attorney, Agent, or Firm*—Woodard, Emhardt, Naughton, Moriarty & McNett

[57] ABSTRACT

Transverse connector (10) bridges rod connector assemblies (40 and 70), and includes an elongate body (12) along longitudinal axis (L). A first portion (20) is formed at a first end (22) of elongate body (12), and has an interlocking surface (26) configured to engage rod connector assembly 40 in variable rotational positions which need not be perpendicular to rod (R1). A second portion (30) is formed at an opposite second end (32) of elongate body (12) and has interlocking surface (36) configured to engage rod connector assembly (70) in variable linear positions. As a result, transverse connector (10) accommodates variable spacing of rods (R1 and R2), and variable positioning of rod connector assemblies (40 and 70) thereon. Rod connector assemblies (40 and 70) include bone screw plates (50 and 80), respectively, connected thereto. A spinal fixation system results which permits connection of a transverse connector (10) at the same site along a rod as a vertebral fixation element.

43 Claims, 4 Drawing Sheets

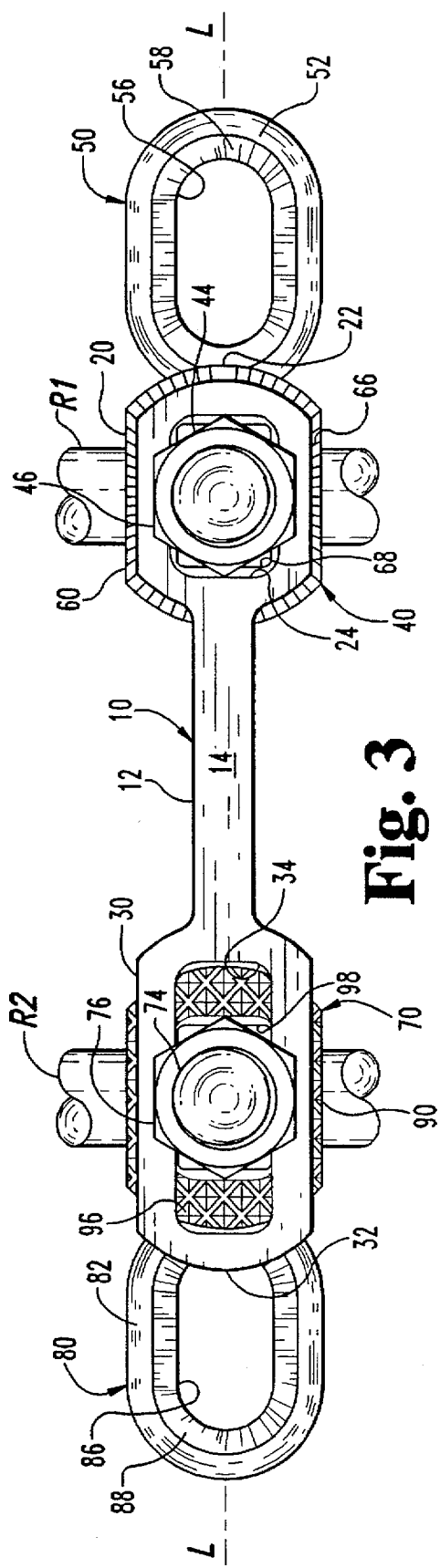
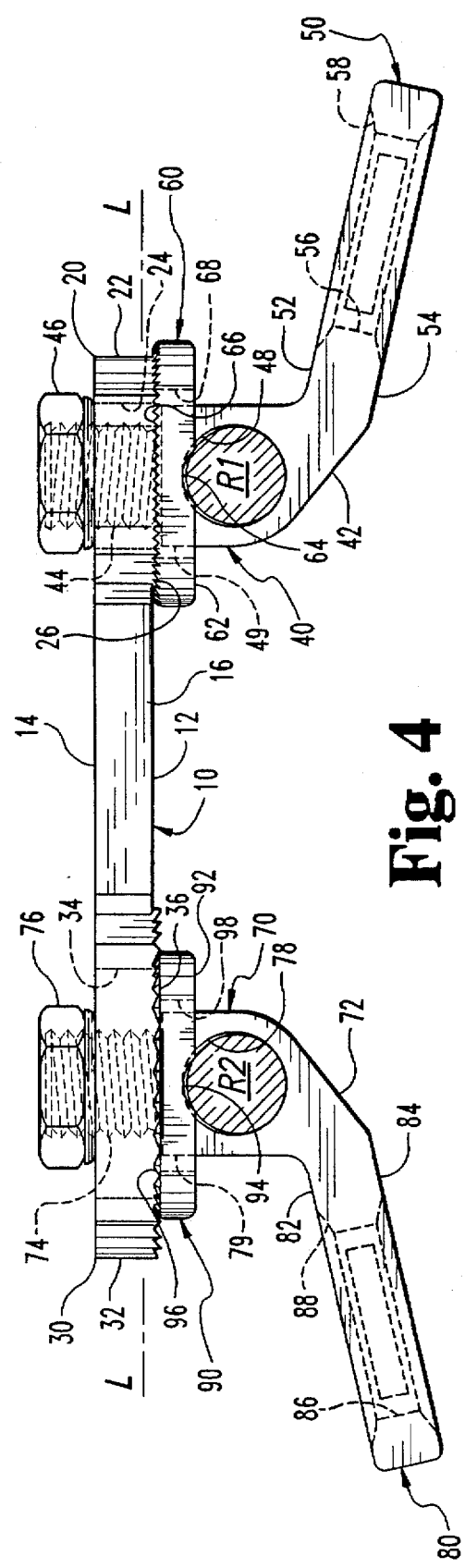
Fig. 3
Fig. 4

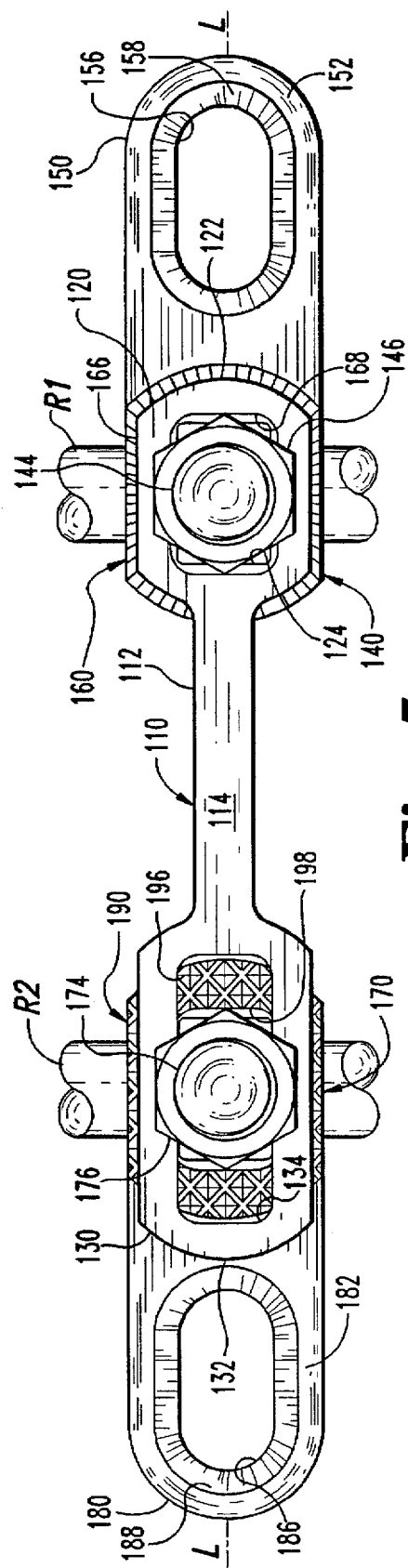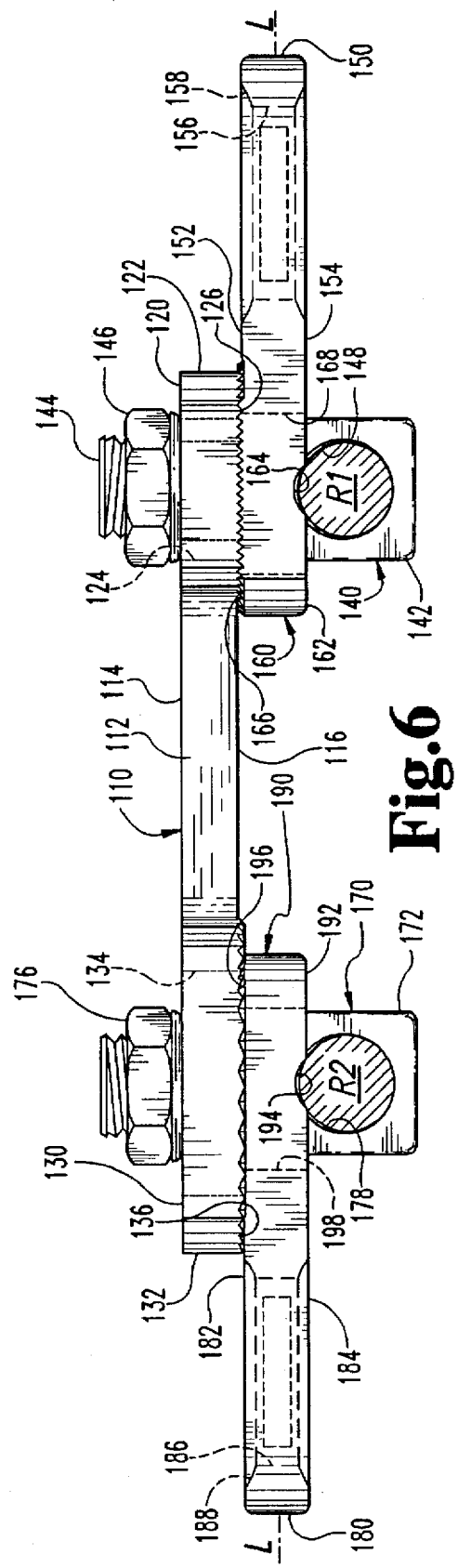

VARIABLE ANGLE AND TRANSITIONAL LINKING MEMBER

BACKGROUND OF THE INVENTION

The present invention concerns spinal fixation systems, and particularly, orthopedic devices which bridge two approximately parallel longitudinal members, such as spinal rods, to enhance construct rigidity.

Spinal fixation systems are implanted during a surgical procedure to treat a variety of problems. These treatments include correction of congenital spinal deformities, repair of spinal injuries, and fusion of vertebrae to stabilize degenerative conditions and alleviate chronic lower back pain. Several techniques and systems have been developed for correcting and stabilizing the spine and facilitating spinal fusion.

In one common system, a longitudinal member, such as a bendable rod, is disposed along the vertebral column and is fixed to various vertebrae along the length of the column by way of a number of fixation elements. A variety of these vertebral fixation elements can be provided, such as hooks or bone screws, which are configured to engage specific portions of the vertebrae. Usually, the surgeon attaches the vertebral fixation elements to the spine in appropriate anatomic positions, and then attaches each vertebral fixation element to the spinal rod. In some systems, a plate with an opening configured to receive a bone screw anchors the base of the spinal fixation system to the sacrum as exemplified by U.S. Pat. Nos. 4,773,402 to Asher et al. and 5,127,912 to Ray et al. which are hereby incorporated by reference.

Commonly, two or more rods are used, each with a number of vertebral fixation elements. Typically, two nearly parallel rods are employed, one on each side of the spinous processes of the vertebral column, and with each end terminating over the sacral region. These terminating ends may be fastened to the sacrum using the aforementioned plate and sacral bone screw vertebral fixation element configuration.

For some existing spinal fixation systems, the vertebral fixation element attaches to a separate fastener carried on the longitudinal member. One such system uses eyebolts as the separate fastener as exemplified by U.S. Pat. Nos. 5,246,442 to Ashman et al. and 5,261,909 to Sutterlin et al. which are hereby incorporated by reference. Other separate fastener systems are shown in U.S. Pat. Nos. 5,024,213 and 4,987,892. Conversely, the body for connecting to the longitudinal member may be integrally formed as part of the vertebral fixation element as disclosed in U.S. Pat. Nos. 5,147,360, 5,005,562, and 4,950,269.

Unfortunately, some clamping assemblies require extensive access to the side of the assembly site to manipulate and tighten clamps. Because surgical access is ordinarily from the posterior of the patient, this "side-tightening" presents some difficulties. Specifically, the threaded stem of the eyebolt and nut engaging this stem both project laterally away from the rod. It has been found that it is often cumbersome to engage the nut with a wrench to tighten the nut onto the eyebolt assembly. Moreover, simple mechanics dictates that the wrench can only be moved with a partial turn before the handle of the wrench contacts the surrounding tissue. This situation necessitates repeated removal of the wrench and re-engagement of the nut to obtain proper adjustment. Ratchet-type wrench systems are typically not acceptable in procedures of this sort because the lateral space required for the ratchet mechanism unnecessarily impinges on the surrounding tissue and requires greater space at the surgical site. Consequently, a subsequent improvement to eyebolt systems is disclosed in U.S. Pat. No. 5,282,801 to Sherman which is hereby incorporated by reference. This improvement clamps a vertebral fixation element and rod together by way of a three-point shear clamp assembly. Notably, this assembly is "top-tightening" because a set screw, completely accessible from the top, is used to initiate and adjust the clamping of the components.

Spinal procedures are rapidly becoming prevalent surgeries, largely because of the high incidence of low back pain. In the past, surgical techniques for alleviating low back pain or for addressing deformities or injuries has required fairly complicated and massive surgical procedures. The focus in recent times has been to greatly reduce the degree of invasion into patients required for stabilizing the spine with instrumentation, as well as to reduce the amount of trauma to tissue surrounding the instrumentation, both during and after the spinal instrumentation has been implanted. Moreover, implants which are easy to assemble and adjust and that provide a rigid construct substantially reduce the risk of complications adversely affecting a patient.

It is a primary goal of the surgeon using a spinal implant system to obtain maximum construct rigidity. Thus, once two rods are fixed to various vertebral fixation elements along the spine, the surgeon may engage a rigid transverse connector to the rods. The connector bridges the rods to form a stable "ladder" or "scaffold" structure.

In one method, an adjustable transverse rod is used to connect the two main rods as shown in U.S. Pat. No. 5,005,562 to Cotrel. For this configuration, the transverse connector site along the rod is separate from the vertebral fixation element fastening site. As a result, the transverse connector requires additional space along the length of the rod which limits the possible construct configurations, and increases size and bulkiness of this construct. This increase in size and bulkiness complicates the implantation procedure and is especially troublesome for implantation into pediatric patients. Also, in patients with severe deformities of the spinal column, the vertebral fixation element sites are often severely limited, so connection flexibility is paramount. Finally, this transverse rod does not provide the desirable top-tightening capability.

The "TSRH® Surgical Manual" hereby incorporated by reference, illustrates a rigid transverse bar, sold as the CROSSLINK® plate, which fastens to rods by way of eyebolts. Similar to the vertebral fixation element attachment, an eyebolt is strung on each rod prior to clamping. The transverse connector receives the threaded stem of the eyebolt through an opening on opposing ends of the connector. A nut is then threaded on each stem to clamp the transverse connector between the nut and the rod at each opposing end. Although this assembly permits top-tightening of the associated clamp, it requires anticipating the placement of additional dedicated eyebolts prior to clamping the vertebral fixation elements to the rod. Also, it still suffers from the size, bulkiness, and "rod crowding" constraints of other systems because it does not facilitate connection at the same site as the vertebral fixation element.

These existing transverse connector devices have opposing ends each with an attachment point for fastening to a rod. Generally, these existing systems only permit attaching the transverse connector to the rods situated a specific distance apart, requiring several such transverse connectors of different lengths for different vertebral levels. Moreover, the transverse connector of existing systems generally requires attachment to the rod at a perpendicular angle. Thus, existing systems notably do not provide variable rotational and linear positioning of the transverse connector with respect to the rod or longitudinal members to be bridged.

A need has remained for spinal systems which provide stable, rigid constructs while allowing a variable range of rotational and linear positions to enhance flexibility of the spinal fixation system configuration.

SUMMARY OF THE INVENTION

In accordance with the present invention, a transverse connector is provided for bridging a first spinal rod carrying a first eyebolt fastening assembly and a second spinal rod carrying a second eyebolt fastening assembly. The connector can be fastened in variable rotational and linear positions. The transverse connector comprises an elongate body along a longitudinal axis, the elongate body having an upper surface and an opposite lower surface. The elongate body includes a first portion formed at one end of the elongate body. The first portion defines a first opening through the upper and lower surfaces and has a first interlocking surface configured to secure the first portion in variable rotational positions when the first portion is fastened to the first spinal rod by the first eyebolt assembly. Also, the elongate body includes a second portion formed at an opposite end of the elongate body. The second portion defines a second opening through the upper and lower surface and has a second interlocking surface configured to secure the second portion in variable linear rotational positions when the second portion is fastened to the second spinal rod by the second eyebolt assembly.

The transverse connector accommodates variable positions between the first and second spinal rods and the first and second eyebolt assemblies. Specifically, when the first portion is fastened to the first spinal rod by the first eyebolt assembly, it can be moved into a rotational position with its longitudinal axis spanning the linear distance separating the first and second eyebolt assemblies. The second portion can then be fastened to the second spinal rod by the second eyebolt assembly. In one preferred embodiment, the first interlocking surface and the first mating surface have interdigitating radial serrations to permit rotational variation, and the second interlocking surface and the second mating surface are knurled to permit both linear and rotational variations.

Still another aspect of the present invention is a spinal fixation system which includes a fastener for fastening a bone screw plate and a transverse connector at the same site along a spinal rod. The spinal fixation system comprises a spinal rod configured for placement adjacent the spine of a patient and a spacer defining an orifice therethrough. The spacer has a spacer surface configured for engaging the spinal rod.

The system also comprises a transverse connector which includes an elongate body along a longitudinal axis. The elongate body has an upper surface and an opposite lower surface, and includes a first portion formed at one end of the elongate body which defines a first opening through the upper and lower surfaces. The elongate body also includes a second portion formed at an opposite end of the elongate body, with a second portion that defines a second opening through the upper and lower surfaces.

A first spinal rod connector can be provided having a passage configured to receive the spinal rod and a threaded stem configured to extend through the orifice of the spacer and the first opening in the transverse connector. In addition, a nut is configured to engage the threaded stem to fasten the transverse connector, the first spacer, and the spinal rod together when the nut is threaded thereon.

Furthermore, a plate is connected to one of the first spacer and the first spinal rod connector, and extends laterally away from the first spinal rod. The plate has a top surface and an opposite bottom surface which define an aperture therethrough configured to receive a bone screw for engagement with the spine.

Accordingly, it is a primary object of the present invention to provide a transverse connector which includes the ability to fasten to longitudinal members adjacent the spine of a patient in variable rotational and linear positions.

Another object of the present invention is to provide a transverse connector which bridges two rods and fastens to each at the same location along the rod as a vertebral fixation element.

Still another object of the present invention is to offer top-tightening for transverse connector fasteners and the vertebral fixation elements connecting at the same site.

Further objects, features, and advantages of the present invention shall become apparent from the detailed drawings and descriptions which follow.

BRIEF DESCRIPTION OF THE DRAWINGS

FIG. 3 is a top plan view of the transverse connector fastened to the rod connector assemblies shown in FIG. 1.

FIG. 4 is a side elevational view of the embodiment shown in FIG. 3.

FIG. 5 is a top plan view of an alternative embodiment of the present invention.

FIG. 6 is a side elevational view of the embodiment shown in FIG. 5.

DESCRIPTION OF THE PREFERRED EMBODIMENT

Figure 1:
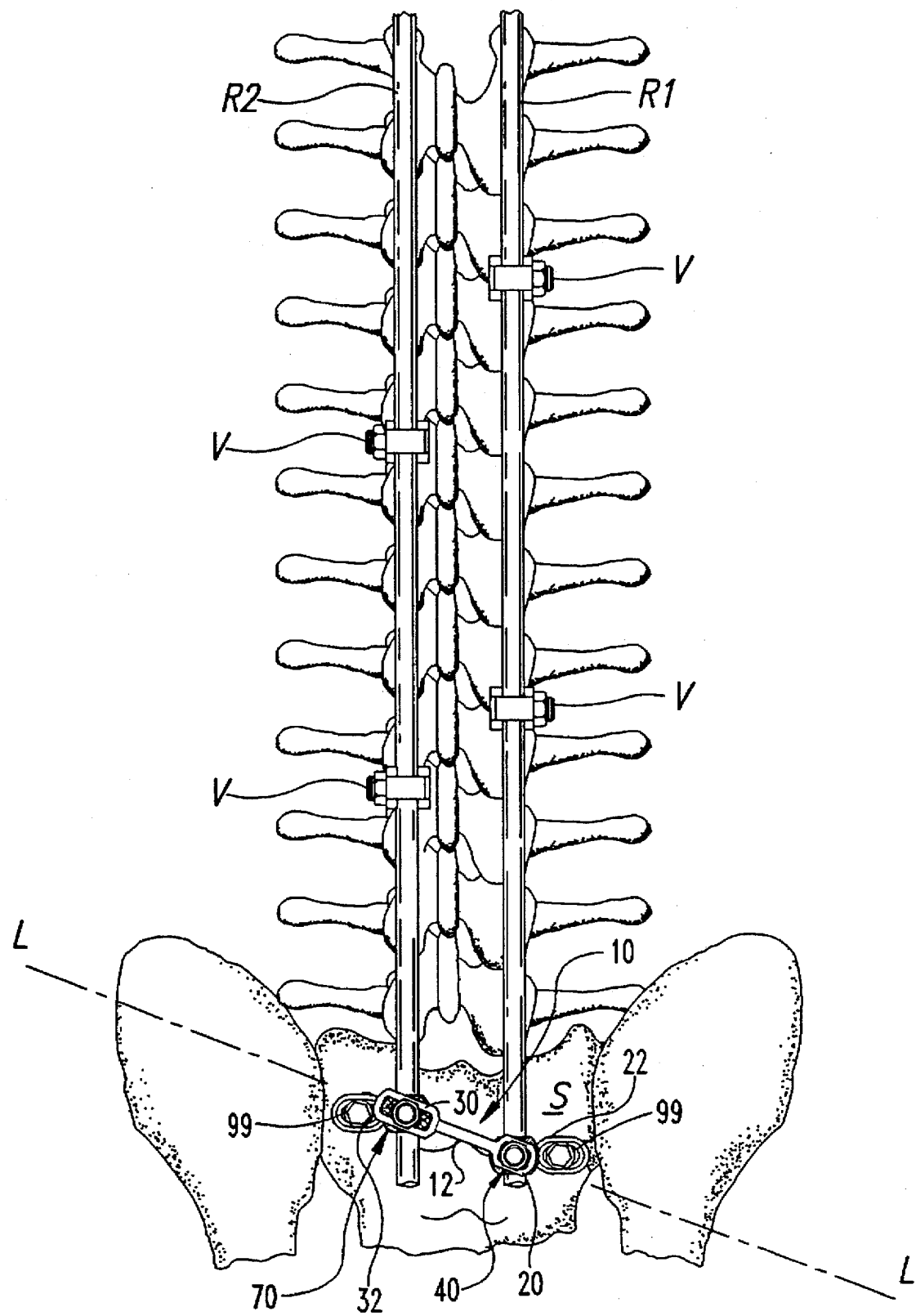
FIG. 1 is a posterior elevational view of one embodiment of the spinal fixation system of the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention is useful for internal fixation of the spine which is indicated for correcting and stabilizing spinal curvatures and for facilitating spinal fusion in the case of spinal disorders or degenerative conditions. This invention provides a top-loaded, top-tightening, low profile spinal fixation system which requires minimal instrumentation yet provides a stable, rigid construct that restricts rod migration and increases overall construct rigidity. The systems include transverse connecting members which span between longitudinal members engaged to the spine to increase construct stability. The transverse connecting members are provided with linear and radial adjustment means for a custom fit to the particular patient, spinal anatomy and condition. These adjustment means permit engagement of the opposite ends of the connecting members to the longitudinal members at different vertebral levels. The invention also includes lateral connector elements which connect the transverse connecting members to both the longitudinal members and vertebral fixation elements at the same vertebral level.

Referring to FIG. 1, a spinal fixation system of the present invention is illustrated. Two approximately parallel spinal rods R1, R2 are shown adjacent the spine of a patient. Among the means fixing the system to the spine are vertebral fixation elements V which are clamped to rods R1 and R2 as shown. Vertebral fixation elements V can include spinal hooks and bone screws. A transverse connector 10 can be positioned towards the base or inferior portion of the spinal fixation system bridging the spinal rods R1 and R2 and fastened by rod connector assemblies 40, 70. Each of the rod connector assemblies 40, 70 includes a suitable fixation element 99 which secures the spinal fixation system to the sacrum S. Any suitable fixation element, such as a bone screw, is contemplated. The transverse connector 10 of the present invention can also be adapted for placement at other vertebral levels.

Transverse connector 10 includes an elongated body 12 along longitudinal axis L. A first portion 20 is formed at a first end 22 of elongate body 12, and a second portion 30 is formed at a second end 32 thereof. Preferably the first portion 20 fixes transverse connector 10 in a rotational position which is not generally perpendicular to rods R1 and R2. Furthermore, second portion 30 accommodates both linear and a rotational positioning to span the distance separating rod connector assemblies 40 and 70. Moreover, transverse connector 10 fastens to rods R1 and R2 at the same site as the fixation element 99.

Figure 2:
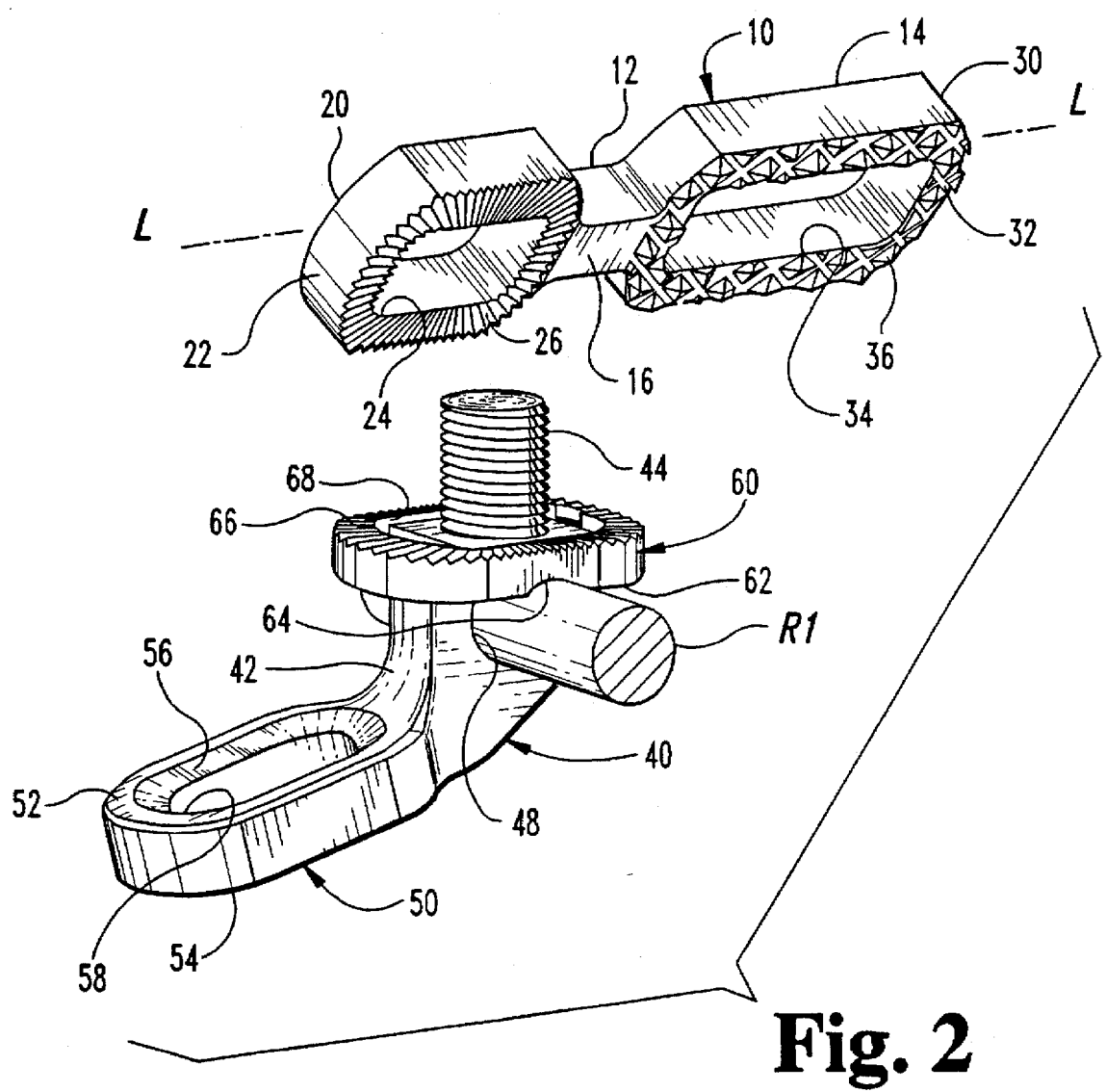
FIG. 2 is an exploded perspective view of the transverse connector and one rod connector assembly for the embodiment shown in FIG. 1.

Referring to FIG. 2, transverse connector 10 and rod connector assembly 40 are shown in more detail. Transverse connector 10 includes an upper surface 14 and an opposite lower surface 16. A first portion 20 formed at one end 22 defines a first opening 24 through upper surface 14 and lower surface 16. Preferably, a portion of lower surface 16 is configured with an interlocking surface 26. Interlocking surface 26 provides a way to lock first portion 20 in a selected rotational position with respect to rod connector assembly 40. Consequently, first portion 20 can act as a rotational portion permitting a variable range of rotational positions of the first portion 20 with respect to rod R1 when fastened by rod connector assembly 40.

Similarly, a second portion 30 is formed at end 32 defining second opening 34 through upper surface 14 and lower surface 16. Preferably, a portion of lower surface 16 is formed with second interlocking surface 36 to allow rotational positioning. Second interlocking surface 36 is also configured to secure second portion 30 at any given linear distance along opening 34. Most preferably opening 34 is configured as an elongate slot with a length along axis L to accommodate various linear positions of a fastener or connector therein. Thus, second portion 30 behaves as a linear translational portion, permitting a variable range of linear positions of the second portion 30 with respect to rod R2 when fastened thereto, while simultaneously permitting connector 10 to assume variable angles relative to the rod R1.

Referring to FIGS. 2–4, connector assembly 40 includes rod connector 42 defining a passage 48 configured to receive rod R1. The passage 48 preferably is slightly larger in diameter than rod R1. Integrally connected to rod connector 42 is plate 50 having upper surface 52 and opposite lower surface 54 defining aperture 56 therethrough. Also, upper surface 52 defines beveled edge 58 around aperture 56. Aperture 56 and beveled edge 58 are preferably configured to receive a conical or spherical portion of a bone screw for securing rod connector assembly 40 and connected fixation system to the spine of a patient.

Rod connector assembly 40 is provided with means for engaging assembly 40 to transverse connector 10. In one specific embodiment, the means for engaging includes threaded stem portion 44 configured to engage a fastener, such as nut 46. Preferably, rod connector assembly 40 also includes spacer 60 having first spacer surface 62 configured to engage rod R1. Specifically, spacer surface 62 defines groove 64 for engaging rod R1. Groove 64 is preferably formed at a diameter smaller than the diameter of the rod to achieve a solid clamping of rod R1. The opposite surface of spacer 60 defines a mating surface 66 that is configured to intermesh with interlocking surface 26 of first portion 20 for interlockingly engagement. For the embodiment shown, interlocking surface 26 and corresponding mating surface 66 have interdigitating radial serrations or splines to secure first portion 20 in variable rotational positions. For other preferred embodiments, other interlocking textures may be employed as are known to those skilled in the art. An orifice 68 is defined between surfaces 62 and 66 that is sized so that threaded stem portion 44 is extendable therethrough. In one embodiment, orifice 68 is also preferably configured to receive portion 49 of rod connector 42 when rod connector assembly 40 is engaged to rod R1 and transverse connector 10. This configuration prevents rotation of spacer 60 about threaded stem portion 44.

Referring to FIGS. 3 and 4, an embodiment is shown with rod connector assembly 70 opposite assembly 40 along transverse connector 10. In this embodiment, rod connector 70 clamps portion 30 of transverse connector 10 and rod R2 together. Assembly 70 includes rod connector 72. Connector 72 may be configured similarly to connector 42 as shown in FIGS. 3 and 4 or varied as would occur to one of skill in the art. In one embodiment, spacer 90 of rod connector assembly 70 is provided with knurled mating surface 96 to provide both linear and rotational adjustments. Mating surface 96 can also be knurled to intermesh with the knurling of interlocking surface 36 of second portion 30 so that interlocking surface 36 and mating surface 96 interlockingly engage each other. For the embodiment shown, this knurling preferably includes pyramidal or diamond shaped asperities. In other preferred embodiments, different knurled textures may be employed as would occur to those skilled in the art, provided that the interlocking textures can achieve linear and rotational variations.

In one embodiment, orifice 98 of spacer 90 preferably is configured to receive a portion 79 of rod connector 72 when rod connector assembly 70 is engaged to rod R2 and transverse connector 10. This configuration prevents rotation of spacer 90 about threaded stem portion 74. Spacer 90 also includes spacer surface 92 opposite mating surface 96. Spacer surface 92 defines groove 94 for engaging rod R2.

Also, in one embodiment, rod connectors 72, 42 each include an integrally connected plate 80, 50 with upper surface 82, 52 and an opposing lower surface 84, 54. In addition, the spacers 60, 90 are staked onto the connectors 42, 72 when provided to the surgeon. In other words the upper edge of the portion 49, 79 of the connectors is staked to hold the spacers 60, 90 in position.

The linear and rotational adjustments allow the surgeon to customize the system. The rotational adjustment means allows engagement of the transverse connector to connecting members attached at different vertebral levels. This allows the surgeon to avoid certain parts of the spinal anatomy which may have defects. It also reduces the amount of bone which must be excised to fit the implant in some cases. Aperture 86, 56 is defined through each of plates 42, 72 which communicate with upper surface 82, 52 and lower surface 84, 54. Upper surface 82, 52 may also define a beveled edge 88, 58 around aperture 86, 56. Plates 80, 50 are usable at various positions on either rod R1 or R2.

For both assemblies 40 and 70, plates 50 and 80 are connected to rod connectors 42 and 72, and extend at a downward angle toward the anterior of a patient and laterally away from rods R1 and R2, respectively. This downward angle is measured between a plane containing the respective plate 50 or 80 and a plane along the posterior or back of a patient. Also, apertures 56 and 86 of plates 50 and 80 respectively, are elongate with a length generally along an axis perpendicular to the longitudinal axis of rods R1 and R2.

Referring specifically to FIG. 4, the manner of assembly of one embodiment of the present invention is discussed. During a surgical procedure, rod connectors 42, 72 are first threaded on rods R1, R2 through respective passage 48, 78. Besides rod connectors 42, 72, other clamps or fasteners for vertebral fixation elements may be carried on rods R1 and R2 to engage the rods to the spine. Next, each connector 42, 72 is positioned along the spine in a convenient location by a surgeon to attach each respective plate 50, 80 to a desired location along the spine using a fastener, such as a bone screw. Once these locations are determined and the respective plates 50, 80 are secured to the spine, spacer 60 is placed over threaded stem 44 of the first rod connector 42 so that groove 64 engages rod R1. Likewise, spacer 90 is placed over threaded stem 74 of rod connector 82 so that groove 94 engages rod R2. Transverse connector 10 is then positioned with first portion 20 over spacer 60 so that threaded stem portion 44 extends through opening 24. First portion 20 may be rotated about threaded stem portion 44 to align transverse connector 10 with the position of the other rod connector assembly 70 positioned along rod R2. Elongate body 12 can be positioned so that axis L generally coincides with a linear distance separating rod connector assembly 40 on rod R1 and rod connector assembly 70 on rod R2. Consequently, when second portion 30 is placed over spacer 90, threaded stem portion 74 occupies a position along opening 34 corresponding to this linear distance separating the rod connector assemblies 40 and 70. The elongate slot configuration of opening 34 permits a variable range of linear positions of threaded stem portion 74 extending therethrough.

The rotational position of first portion 20 placed on spacer 60 is secured by threading nut 46 on threaded stem portion 44 protruding through orifice 68 and opening 24. As nut 46 is threaded on threaded stem portion 44, transverse connector portion 20 is clamped between nut 46 and spacer 60. Furthermore, spacer 60 is clamped between transverse connector 10 and rod R1. Also, rod R1 is clamped between spacer 60 and a wall of passage 48. Thus, as nut 46 is tightened on threaded stem portion 44, rod connector assembly 40 becomes rigidly clamped to transverse connector 10 and rod R1. Moreover, as nut 46 is tightened, interlocking surface 26 and mating surface 66 engage each other so that corresponding serrations interdigitate to secure the selected rotational position of first portion 20.

Likewise, nut 76 is threaded on threaded stem portion 74 to clamp second portion 30 of transverse connector 10 between nut 76 and spacer 90. Also, spacer 90 is clamped between second portion 30 and rod R2. Moreover, rod R2 is clamped between spacer 90 and a wall of passage 78 of rod connector 72. Notably, as nut 76 is threaded on threaded stem portion 74, the knurled surface of interlocking surface 36 and mating surface 96 engage each other so that the asperities of the knurled surfaces can be deformed and crushed together to secure the linear and angular position of second portion 30. Alternatively, the asperities of the respective knurled surface can interdigitate to secure the position.

In other preferred embodiments, one or more of openings 24 and 34, or apertures 56 and 86 may be configured as an open slot or notch instead of a closed bore or hole as shown in FIGS. 1–4. In another preferred embodiment, it is envisioned that rod connector 10 may be connected to other types of spinal fixation systems which use a longitudinal plate or similarly configured longitudinal member in place of a rod. Longitudinal plates are exemplified by U.S. Pat. No. 4,790,297 to Luque which is hereby incorporated by reference. It is envisioned that the plate could be configured with corresponding mating surfaces to provide for variable rotational and linear positioning of transverse connector 10.

In still other preferred embodiments, transverse connector 10 can be connected to a longitudinal member using other means. For example, instead of a threaded stem portion, a threaded bore defined by the connector body could be configured to receive a correspondingly threaded bolt with a head that functions similar to the nut. In still other embodiments, a different type of rod clamp may be used to fasten the transverse connector of the present invention to a rod. Specifically, U.S. Pat. No. 5,282,801 to Sherman illustrates a rod clamp that uses a set screw to fasten the rod to the clamp assembly. This clamp assembly could be modified by extending the length of the set screw with a threaded stem portion to extend through either of the openings of the first and second portions of the transverse connector of the illustrated embodiment. Similarly, the clamp assembly could be configured with a mating surface to interlockingly engage an interlocking surface of the transverse connector. Thus, the present invention contemplates a variety of connector means for fastening the transverse connector to a longitudinal member.

An alternative embodiment of the present invention is depicted in FIGS. 5 and 6. In this embodiment, transverse connector 110 includes elongate body 112 along a longitudinal axis L. Transverse connector 110 has an upper surface 114 opposing a lower surface 116. Rotational first portion 120 is formed at one end 122, while linear translational and rotational second portion 130 formed at the opposite end 132. First portion 120 defines an opening 124 through upper surface 114 and lower surface 116, and has interlocking surface 126. Second portion 130 defines opening 134 through upper surface 114 and lower surface 116 and has interlocking surface 136.

A rod connector assembly 140 is engageable to first portion 120. Rod connector assembly 140 includes a rod connector 142 defining passage 148 configured to receive rod R1. Rod connector 142 also has threaded stem portion 144 configured to protrude through spacer 160 and opening 124 of first portion 120. In this embodiment, spacer 160 is integrally connected to plate 150. Plate 150 has top surface 152 opposing lower surface 154, and each of these surfaces define an aperture 156 therethrough. Preferably, a beveled edge 158 is defined by upper surface 152 around aperture 156.

Spacer 160 includes spacer surface 162 configured to engage rod R1, and preferably, defines a groove 164 to engage rod R1. Opposing spacer surface 162 has a mating surface 166 configured for interlocking engagement with interlocking surface 126 of first portion 120. Surfaces 162 and 166 define orifice 168 therethrough.

Rod connector assembly 170 includes rod connector 172 defining passage 178 configured to receive rod R2. Rod connector 172 includes threaded stem portion 174 configured to protrude through orifice 198 of spacer 190 and opening 134 of second portion 130. Spacer 190 includes plate 180 integrally connected thereto. Plate 180 has top surface 182 opposing lower surface 184 and defining aperture 186 therethrough. Beveled edge 188 around aperture 186 is also defined by top surface 182. Spacer 190 has a spacer surface 192 configured to engage rod R2, and specifically, defining groove 194 to engage rod R2. Opposing spacer surface 192, is mating surface 196 configured for interlocking engagement with interlocking surface 136 of second portion 130. Surfaces 192 and 196 define orifice 198 therethrough.

Assembly of the embodiment shown in FIGS. 5 and 6 is similar to assembly of the embodiment shown in FIGS. 1-4. As transverse connector 110 is clamped between nut 146 and spacer 160, the interdigitating serrations of interlocking surface 126 and 166 interlockingly engage to secure first portion 120 in a desired rotational position. As a fastener, such as nut 176, is threaded on threaded stem portion 174, transverse connector 110 is clamped against spacer 190 and knurled interlocking surface 136 and mating surface 196 interlockingly engage to secure second portion 130 in a desired linear position and angular position.

The devices of the present invention are preferably formed of medical grade stainless steel, titanium, or any other biocompatible, high strength material. Specifically, the devices could be manufactured in 316LVM stainless steel or ASTM F-136 titanium (T16AL-AV). The devices can be provided in any size which is suitable to the particular patient, medical condition and vertebral level. In a particular embodiment, the spinal rod connector is about 2-5 inches (6.2 cm) long.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. A spinal fixation system, comprising:
   a first spinal rod configured for placement adjacent the spine of a patient;
   a first spacer defining a first orifice therethrough, and having a first spacer surface configured for engaging said first spinal rod;
   a transverse connector including an elongated body along a longitudinal axis, said elongated body having an upper surface and an opposite lower surface, and including;
      a first portion formed at one end of said elongated body, said first portion defining a first opening through said upper and lower surfaces; and
      a second portion formed at an opposite end of said elongate body, said second portion defining a second opening through said upper and lower surfaces;
   a first spinal rod connector defining a passage configured to receive said first spinal rod therethrough and having a first stem portion configured to extend through said first orifice of said first spacer and said first opening of said transverse connector with said first spacer surface of said first spacer engaging said first rod;
   a first fastener configured to engage said first stem portion to clamp said first spacer between said first portion of said transverse connector and said first spinal rod when said first fastener is engaged on said first stem portion; and
   a first plate connected to one of said first spacer and said first spinal rod connector and extending away from said first spinal rod, said first plate defining a first aperture therethrough configured to receive a bone fastener therethrough for engagement with the spine.

2. The spinal fixation system of 1, wherein said first plate has a top surface opposing a bottom surface, said top surface defines a beveled edge around said first aperture of said first plate, and said first aperture is elongated.

3. The spinal fixation system of 1, wherein said first plate is connected to said first spinal rod connector and extends away from said first spinal rod at a downward angle.

4. The spinal fixation system of 1, wherein said first plate is connected to said first spacer.

5. The spinal fixation system of claim 1, further comprising:
   a second spinal rod spaced apart from said first spinal rod;
   a second spacer defining a second orifice therethrough, and having a second surface configured to engage said second spinal rod;
   a second spinal rod connector defining a passage configured to receive said second spinal rod therethrough and having a second stem portion configured to extend through said second orifice of said second spacer and said second opening of said transverse connector with said second spacer surface of said second spacer engaging said second rod;
   a second fastener configured to engage said second stem portion to clamp said second spacer between said first portion of said transverse connector and said second spinal rod when said second fastener is engaged on said second stem portion; and
   a second plate connected to one of said second spacer and said second spinal rod connector and extending away from said second spinal rod, said second plate defining a second aperture therethrough configured to receive a bone fastener therethrough for engagement with the spine.

6. The spinal fixation system of claim 1, wherein said second portion has a second interlocking surface and said second spacer has a second mating surface configured to engage said second interlocking surface to secure said second portion in variable linear and rotational positions relative to said second spacer.

7. The spinal fixation system of claim 6, wherein said second interlocking surface and said second mating surface are knurled.

8. The spinal fixation system of claim 7, wherein:
   said first portion has a first interlocking surface and said first spacer has a first mating surface configured to engage said first interlocking surface to secure said first portion in variable rotational positions relative to said first spacer.

9. The spinal fixation system of claim 8, further comprising a first plurality of vertebral fixation elements clamped to said first spinal rod and a second plurality of vertebral fixation elements clamped to said second spinal rod, and wherein:
   said first interlocking surface and said first mating surface have interdigitating serrations;

said second opening is configured as an elongate slot having a length along the longitudinal axis;

said first spacer surface defines a first groove to engage said first spinal rod, said first spacer surface opposing said first mating surface;

said second spacer surface defines a second groove to engage said second spinal rod, said second spacer surface opposing said second mating surface;

said first plate is connected to said first spinal rod connector and extends away from said first spinal rod at a downward angle;

said second plate is connected to said second spinal rod connector and extends away from said second spinal rod at a downward angle; and said first and second apertures are elongate.

10. A spinal fixation system, comprising:

a first spinal rod configured for placement adjacent the spine of a patient;

a first spacer defining a first orifice therethrough, and having a first spacer surface configured for engaging said first spinal rod;

a transverse connector including an elongated body along a longitudinal axis, said elongated body having an upper surface and an opposite lower surface, and including;
  a first portion formed at one end of said elongated body, said first portion defining a first opening through said upper and lower surfaces; and
  a second portion formed at an opposite end of said elongate body, said second portion defining a second opening through said upper and lower surfaces;

a first connector means carried on said first spinal rod and having means for clamping said first portion and said first spinal rod in a fixed position on said rod;

a first plate connected to one of said first spacer and said first connector means and extending away from said first spinal rod, said first plate defining a first aperture therethrough configured to receive a bone fastener therethrough for engagement with the spine.

11. The spinal fixation system of 10, wherein said first plate has a top surface opposing a bottom surface, said top surface defines a beveled edge around said first aperture of said first plate, and said first aperture is elongated.

12. The spinal fixation system of 10, wherein said first plate is connected to said first connector means and extends away from said first spinal rod at a downward angle.

13. The spinal fixation system of claim 10, wherein said first plate is connected to said first spacer.

14. The spinal fixation system of claim 10, wherein said first portion has a first interlocking surface and said first spacer has a first mating surface configured to engage said first interlocking surface to secure said first portion in variable linear and rotational positions relative to said first spacer.

15. The spinal fixation system of claim 10, further comprising:
  a second spinal rod spaced apart from said first spinal rod;
  a second connector means carried on said second spinal rod and having means for clamping said second portion and said second spinal rod in a fixed position on said second spinal rod;
  a second plate connected to one of said second spacer and said second connector means and extending away from said second spinal rod, said second plate defining a second aperture therethrough configured to receive a bone fastener therethrough for engagement with the spine.

16. A spinal fixation system, comprising:

a first longitudinal member configured for placement adjacent the spine of a patient:

a second longitudinal member spaced apart from said first longitudinal member, said second longitudinal member being configured for placement adjacent the spine of a patient:

a transverse connector including an elongated body along a longitudinal axis, said elongated body having an upper surface and an opposite lower surface, and including;
  a first portion formed at one end of said elongated body, said first portion defining a first opening through said upper and lower surfaces, said first portion having a first interlocking surface; and
  a second portion formed at an opposite end of said elongate body, said second portion deigning a second opening through said upper and lower surfaces, said second portion having a second interlocking surface;

a first means for fastening said first portion and said first longitudinal member together, said first means having a first mating surface;

first interlocking means between said first interlocking surface and said first mating surface for interlocking said first mating surface with said first interlocking surface in variable rotational positions relative to each other when said first portion and said first longitudinal member are fastened together;

a second means for fastening said second portion and said second longitudinal member together, said second means having a second mating surface; and second interlocking means between said second interlocking surface and said second mating surface for interlocking said second mating surface with said second interlocking surface in variable linear and rotational positions relative to each other when said second portion and said second longitudinal member are fastened together.

17. The spinal fixation system of claim 16, wherein said first means includes a plate connected thereto, said plate extends away from said first longitudinal member, said plate has a top surface and an opposite bottom surface, and said top and bottom surfaces define an aperture therethrough configured to receive a bone fastener for engagement with the spine.

18. The spinal fixation system of claim 16, wherein said first interlocking surface and said first mating surface have interdigitating serrations.

19. The spinal fixation system of claim 16, wherein said second interlocking surface and said second mating surface are knurled.

20. The spinal fixation system of claim 16, wherein said second opening is configured as an elongate slot having a length along the longitudinal axis.

21. The spinal fixation system of claim 20, wherein said first interlocking surface and said first mating surface have interdigitating serrations, and said second interlocking surface and said second mating surface are knurled.

22. The spinal fixation system of claim 16, wherein said second interlocking surface includes a first number of projecting asperities and said second mating surface includes a second number of projecting asperities, said first and second asperities being configured to intermesh.

23. A spinal fixation system, comprising:

a first spinal rod configured for placement adjacent the spine of a patient;

a second spinal rod spaced apart from said first spinal rod, said second spinal rod being configured for placement adjacent the spine of a patient;

a transverse connector including an elongated body along a longitudinal axis, said elongated body having an upper surface and an opposite lower surface, and including;

a first portion formed at one end of said elongated body, said first portion defining a first opening through said upper and lower surfaces, said first portion having a first interlocking surface; and a second portion formed at an opposite end of said elongate body, said second portion defining a second opening through said upper and lower surfaces, said second portion having a second interlocking surface;

a first spacer defining a first orifice therethrough, and having a first spacer surface configured for engaging said first spinal rod and a first mating surface;

first interlocking means for interlocking said first mating surface with said first interlocking surface in variable rotational positions relative to each other;

a first spinal rod connector defining a passage configured to receive said first spinal rod therethrough and having a first stem portion configured to extend through said first orifice of said first spacer and said first opening of said transverse connector with said first spacer surface of said first spacer engaging said first rod;

a first fastener configured to engage said first stem portion to clamp said first spacer between said first portion of said transverse connector and said first spinal rod when said first fastener is engaged on said first stem portion;

a second spacer defining a second orifice therethrough, and having a second surface configured for engaging said second spinal rod and a second mating surface;

second interlocking means for interlocking said second mating surface with said second interlocking surface in variable linear and rotational positions relative to each other;

a second spinal rod connector defining a passage configured to receive said second spinal rod therethrough and having a second stem portion configured to extend through said second orifice of said second spacer and said second opening of said transverse connector with said second spacer surface of said second spacer engaging said second rod; and second fastener configured to engage said second stem portion to clamp said second spacer between said second portion of said transverse connector and said second spinal rod when said second fastener is engaged on said second stem portion.

24. The spinal fixation system of claim 23, wherein said first connector includes a plate connected thereto, said plate extends away from said first spinal rod, said plate has a top surface and an opposite bottom surface, and said top and bottom surfaces define an aperture therethrough configured to receive a bone fastener for engagement with the spine.

25. The spinal fixation system of claim 23, wherein said first interlocking surface and said first mating surface have interdigitating serrations.

26. The spinal fixation system of claim 23, wherein said second interlocking surface and said second mating surface are knurled.

27. The spinal fixation system of claim 23, wherein said second opening is configured as an elongate slot having a length along the longitudinal axis.

28. The spinal fixation system of claim 27, wherein said first interlocking surface and said first mating surface have interdigitating serrations, and said second interlocking surface and said second mating surface are knurled.

29. The spinal fixation system of claim 23, wherein said second interlocking surface includes a first number of projecting asperities and said second mating surface includes a second number of projecting asperities, said first and second asperities being configured to intermesh.

30. A transverse connector for bridging a first longitudinal member carrying a first connector thereon and a second longitudinal member carrying a second connector thereon, comprising:

an elongated body having an upper surface and an opposite lower surface, and a first end and an opposite second end;

a first portion connected to said first end, said first portion defining a first opening through said upper and lower surfaces, said first portion having a first interlocking surface configured to engage a first mating surface on the first connector, said first interlocking surface and the first mating surface having first interlocking means cooperating therebetween for securing said first portion in a first position, said first position being rotationally variable with respect to said first longitudinal member to place said second end proximate to the second longitudinal member;

a second portion connector to said second end, said second portion defining a second opening through said upper and lower surface, said second portion having a second interlocking surface configured to engage a second mating surface on the second connector, said second interlocking surface and the second mating surface having second interlocking means cooperating therebetween for securing said second portion in a second position, said second position being rotationally and translationally variable to correspond to said first position.

31. The transverse connector of claim 30, wherein said transverse connector is symmetric about a plane intersecting said upper and lower surfaces and including the longitudinal axis.

32. The transverse connector of claim 30, wherein said second opening is configured as an elongate slot.

33. The spinal fixation system of claim 30, wherein said first interlocking surface includes radial splines.

34. The spinal fixation system of claim 30, wherein said second interlocking surface in knurled.

35. The spinal fixation system of claim 30, wherein said first interlocking surface includes interdigitating serrations, and said second interlocking surface includes knurling.

36. The transverse connector of claim 35, wherein said second opening is configured as an elongated slot.

37. The transverse connector of claim 36, wherein said elongated slot has a length along a longitudinal axis of said elongated body.

38. The transverse connector of claim 30, wherein said second interlocking surface includes a first number of projecting asperities and said second mating surface includes a second number of projecting asperities, said first and second asperities being configured to intermesh.

39. A spinal fixation system, comprising:

a first longitudinal member configured for placement adjacent the spine of a patient;

a second longitudinal member spaced apart from said first longitudinal member, said second longitudinal member being configured for placement adjacent the spine of a patient;

a transverse connector including an elongated body along a longitudinal axis, said elongated body having an upper surface and an opposite lower surface, and including:
- a first portion formed at one end of said elongated body, said first portion defining a first opening through said upper and lower surfaces, said first portion having a first interlocking surface,
- a second portion formed at an opposite end of said elongate body, said second portion defining a second opening through said upper and lower surfaces, said second portion having a second interlocking surface; and a first fastener connecting said first portion and said first longitudinal member together, said first fastener having a first mating surface configured to interlock with said first interlocking surface to secure said first portion relative to said first longitudinal member, said first interlocking surface being knurled to define a first number of asperities and said first mating surface being knurled to define a second number of asperities, said first and second asperities being configured to intermesh in a plurality of rotational positions relative to each other.

40. The system of claim 39, further comprising a second fastener for connecting said second portion and said second longitudinal member together, said second fastener having a second mating surface configured to interlock with said second interlocking surface to secure said second portion in variable rotational positions relative to each other.

41. The system of claim 40, wherein said second interlocking surface defines a first number of radial splines, said second mating surface defines a second number of radial splines, and said first and second splines are interdigitated.

42. The system of claim 39, wherein said first and second asperities are generally diamond-shaped.

43. The system of claim 39, wherein said first asperities are each separated from the others by a surrounding channel, and said second asperities are each separated from the others by a surrounding channel.

* * * * *

UNITED STATES PATENT AND TRADEMARK OFFICE
CERTIFICATE OF CORRECTION

PATENT NO : 5,693,053
DATED : December 2, 1997
INVENTOR(S) : Bradley T. Estes

It is certified that error appears in the above-identified patent and that said Letters Patent is hereby corrected as shown below:

In column 12, line 17, change "deigning" to --defining--.

Signed and Sealed this

Eighteenth Day of May, 1999

Attest:

Q. TODD DICKINSON

Attesting Officer

Acting Commissioner of Patents and Trademarks